(12) United States Patent
Jones et al.

(10) Patent No.: US 6,909,024 B1
(45) Date of Patent: Jun. 21, 2005

(54) PROCESS FOR THE CONVERSION OF ETHYLENE TO VINYL CHLORIDE AND NOVEL CATALYST COMPOSITIONS USEFUL FOR SUCH PROCESS

(75) Inventors: Mark E. Jones, Midland, MI (US); Michael M. Olken, Midland, MI (US); Daniel A. Hickman, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 148 days.

(21) Appl. No.: 10/130,104

(22) PCT Filed: Oct. 3, 2000

(86) PCT No.: PCT/US00/27272

§ 371 (c)(1),
(2), (4) Date: May 14, 2002

(87) PCT Pub. No.: WO01/38273

PCT Pub. Date: May 31, 2001

Related U.S. Application Data
(60) Provisional application No. 60/166,897, filed on Nov. 22, 1999.

(51) Int. Cl.⁷ .................. C07C 17/013; C07C 17/02; C07C 17/07; C07C 17/08
(52) U.S. Cl. .................. 570/216; 570/224; 570/226; 570/227; 570/228; 570/230
(58) Field of Search ............................. 570/216, 224, 570/226, 227, 228, 230

(56) References Cited

U.S. PATENT DOCUMENTS

| | | | |
|---|---|---|---|
| 2,204,733 A | 6/1940 | Miller | .......................... 23/219 |
| 3,488,398 A | 1/1970 | Harpring et al. | ............ 260/659 |
| 3,629,354 A | 12/1971 | Beard et al. | ............. 260/683.3 |

(Continued)

FOREIGN PATENT DOCUMENTS

| | | | |
|---|---|---|---|
| EP | 0162 457 B1 | 7/1989 | ........... C07C/17/34 |
| EP | 0 372 183 B1 | 1/1997 | ......... C07C/11/107 |
| EP | 0 667 845 B1 | 1/1998 | ......... C07C/17/154 |
| FR | 1 594 693 | 7/1970 | |
| GB | 1 039 369 | 8/1966 | |
| GB | 1 040 962 | 9/1966 | |
| GB | 1 141 369 | 1/1969 | ........... C07C/19/02 |
| GB | 1 213 202 | 11/1970 | ........... C07C/21/06 |
| GB | 1373296 | 11/1974 | ........... C07C/17/10 |
| GB | 1 475 358 | 6/1977 | ........... C07C/17/15 |
| GB | 1 492 945 | 11/1977 | |
| GB | 2 095 242 | 9/1982 | |
| GB | 2 101 596 A | 1/1993 | |
| WO | WO 01/38271 | 5/2001 | |
| WO | WO 01/38272 | 5/2001 | |
| WO | WO 01/38273 | 5/2001 | |
| WO | WO 01/38274 | 5/2001 | |
| WO | WO 01/38275 | 5/2001 | |
| WO | WO 01/42176 | 6/2001 | |

OTHER PUBLICATIONS

Wm. C. Conner, Jr. et al., The Oxyhydrochlorination of Methane on Fumed Silica–Based Cu, K, La Catalysts: III Bulk & Surface Analysis, Applied Catalysis, vol. 11, pp. 59–71, 1984.*
G. Olah et al., Selective Monohalogenation of Methane over Supported Acid or Platinum Metal Catalysts and Hydrolysis of Methyl Halides over γ–Alumina–Supported Metal Oxide/Hydroxide Catalysts. A Feasible Path for the Oxidative Conversion of Methane into Methyl Alcohol/Dimethyl Ether, American Chemical Society, vol. 107, No. 24, pp 7097–7105, 1985.*
E. Fortini et al., Stabilization of the Active Phase by Interaction with the Support in $CuCl_2$ Oxychlorination Catalysts, Journal of Catalysis, vol. 99, pp. 12–18, 1986.*
I. Fells, The Kinetics of the Hydrolysis of the Chlorinate Methanes, Fuel Society Journal, vol. 10, pp. 26–35, 1959.
W. Pieters et al., The Oxyhydrochlorination of Methane on Fumed Silica—Based $Cu^{+1}$, K, La Catalysts: I. Catalyst Synthesis, Applied Catalysis, vol. 11, pp. 35–48, 1984.
Wm. C. Conner, Jr., et al., The Oxyhydrochlorination of Methane on Fumed Silica–Based Cu, K, La Catalysts: II Gas Phase Stoichiometry, Applied Catalysis, vol. 11, pp. 49–58, 1984.
P. Chanaud, et al., Catalytic membrane reactor for oxidative coupling of methane. Part 1: preparation and characterization of LaOCl membranes, Catalysis Today, 25, 1995, pp. 225–230.
P. Chanaud et al., Study of lanthanum–based colloidal sols formation, Journal of Materials Science, 29, 1994, pp. 4244–4251.
C. T. Au et al., The oxidative coupling of methane over $BaCO_3$/LaOCl catalysts, Applied Catalysis A: General, 159, 1997, pp. 133–145.
Bert M. Weckhuysen, et al., Destructive absorption of carbon tetrachloride on lanthanum and cerium oxides, Phys. Chem. Chem. Phys., 1999, 1, pp. 3157–3162.
M. McDonald et al., Effects of Pressure on the Oxyhydrochlorination of Methane, Chemical Engineering Science, vol. 49, No. 24A, pp. 4627–4637, 1994.

(Continued)

Primary Examiner—Elvis O. Price

(57) ABSTRACT

This invention is a process for producing vinyl chloride from an ethylene-containing feed, oxygen, and a chlorine source in the presence of a catalyst. The process permits direct production of vinyl chloride in a single reactor system, and further permits ethane to be used as the $C_2$ hydrocarbon feed with recycle of ethylene from the product stream to constitute the ethylene specified for the feed. This invention in another aspect concerns also a composition of matter, and a method for making the composition, wherein the composition is useful as a catalyst for the vinyl chloride process. The composition comprises a rare earth-containing material, with the proviso that the catalyst prepared therefrom is substantially free of iron and copper and with the further proviso that when cerium is present the catalyst further comprises at least one more rare earth element other than cerium.

26 Claims, No Drawings

U.S. PATENT DOCUMENTS

| | | | |
|---|---|---|---|
| 3,634,330 A | 1/1972 | Yerres et al. | 252/441 |
| 3,644,561 A | 2/1972 | Beard et al. | 260/683.3 |
| 3,657,367 A | 4/1972 | Blake et al. | 260/659 A |
| 3,658,933 A | 4/1972 | Beard et al. | 260/683.3 |
| 3,658,934 A | 4/1972 | Beard et al. | 260/683.3 |
| 3,702,311 A | 11/1972 | Beard et al. | 252/441 |
| 3,769,362 A | 10/1973 | Beard et al. | 260/677 XA |
| 3,927,131 A | 12/1975 | Ward | 260/654 D |
| 3,968,200 A | 7/1976 | Tsao | 423/488 |
| 4,042,640 A | 8/1977 | Tsao | 260/659 |
| 4,046,821 A | 9/1977 | Croce et al. | 260/654 A |
| 4,046,823 A | 9/1977 | Gordon et al. | 260/662 R |
| 4,100,211 A | 7/1978 | Magistro | 260/656 R |
| 4,110,251 A | 8/1978 | Lauder et al. | 252/442 |
| 4,230,668 A | 10/1980 | Sheely et al. | 422/140 |
| 4,300,005 A | 11/1981 | Li | 570/224 |
| 4,319,062 A | 3/1982 | Boozalis et al. | 570/220 |
| 4,323,482 A | 4/1982 | Stiles et al. | 252/462 |
| 4,329,525 A | 5/1982 | Riegel et al. | 570/191 |
| 4,375,569 A | 3/1983 | Kroenke et al. | 570/224 |
| 4,402,942 A | 9/1983 | Melin | 424/177 |
| 4,405,500 A | 9/1983 | Muller et al. | 252/433 |
| 4,460,699 A | 7/1984 | Convers et al. | 502/84 |
| 4,462,970 A | 7/1984 | Pastor et al. | 423/263 |
| 4,528,174 A | 7/1985 | Schmidhammer et al. | 423/488 |
| 4,529,410 A | 7/1985 | Khaladji et al. | 51/309 |
| 4,590,216 A | 5/1986 | Dombek | 518/700 |
| 4,727,201 A | 2/1988 | Cobb | 570/202 |
| 4,737,594 A | 4/1988 | Olah | 570/222 |
| 4,754,088 A | 6/1988 | Schmidhammer et al. | 570/247 |
| 4,766,103 A | 8/1988 | Cobb | 502/217 |
| 4,783,564 A | 11/1988 | Piotrowski et al. | 570/254 |
| 4,849,562 A | 7/1989 | Buhs et al. | 570/241 |
| 4,859,432 A | 8/1989 | David et al. | 423/21.1 |
| 4,899,000 A | 2/1990 | Stauffer | 570/222 |
| 4,942,697 A | 7/1990 | Khaladji et al. | 51/283 R |
| 4,965,057 A | 10/1990 | David et al. | 423/263 |
| 5,008,225 A | 4/1991 | Magistro | 502/73 |
| 5,013,534 A | 5/1991 | Dissaux et al. | 423/263 |
| 5,023,070 A | 6/1991 | Le Loarer | 423/592 |
| 5,061,670 A | 10/1991 | Forquy et al. | 585/500 |
| 5,072,063 A | 12/1991 | Langensee | 570/236 |
| 5,087,791 A | 2/1992 | Magistro | 585/657 |
| 5,097,083 A | 3/1992 | Stauffer | 570/241 |
| 5,099,085 A | 3/1992 | Strasser et al. | 570/245 |
| 5,113,027 A | 5/1992 | Mainz et al. | 570/224 |
| 5,114,702 A | 5/1992 | Pederson et al. | 423/639 |
| 5,137,862 A | 8/1992 | Mackrodt et al. | 502/303 |
| 5,178,664 A | 1/1993 | Picard | 75/300 |
| 5,179,215 A | 1/1993 | Ramachandran et al. | 549/262 |
| 5,210,358 A | 5/1993 | Magistro | 585/500 |
| 5,227,549 A | 7/1993 | Correia et al. | 570/243 |
| 5,232,889 A | 8/1993 | Blanchard et al. | 502/263 |
| 5,262,547 A | 11/1993 | Ramachandran et al. | 549/262 |
| 5,352,646 A | 10/1994 | Blanchard et al. | 502/263 |
| 5,397,758 A | 3/1995 | Bouruetaubertot et al. | 502/303 |
| 5,453,557 A | 9/1995 | Harley et al. | 585/641 |
| 5,466,837 A | 11/1995 | Ramachandran et al. | 549/533 |
| 5,492,878 A | 2/1996 | Fujii et al. | 502/304 |
| 5,496,528 A | 3/1996 | David et al. | 423/263 |
| 5,510,546 A | 4/1996 | Ito | 570/236 |
| 5,580,536 A | 12/1996 | Yao et al. | 423/263 |
| 5,599,588 A | 2/1997 | Poncelet | 427/343 |
| 5,600,042 A | 2/1997 | Chen et al. | 570/224 |
| 5,607,890 A | 3/1997 | Chen et al. | 205/202 |
| 5,646,304 A | 7/1997 | Acharya et al. | 549/259 |
| 5,663,112 A | 9/1997 | Ahn et al. | 502/304 |
| 5,663,465 A | 9/1997 | Clegg et al. | 570/224 |
| 5,663,472 A | 9/1997 | Benson et al. | 585/641 |
| 5,705,728 A | 1/1998 | Viswanathan et al. | 585/641 |
| 5,728,905 A | 3/1998 | Clegg et al. | 570/224 |
| 5,762,894 A | 6/1998 | Takatori et al. | 423/263 |
| 5,763,710 A | 6/1998 | Clegg et al. | 570/224 |
| 5,773,383 A | 6/1998 | Suciu | 502/355 |
| 5,874,380 A | 2/1999 | Chen et al. | 502/217 |
| 5,877,371 A | 3/1999 | Chen et al. | 585/467 |
| 5,880,058 A | 3/1999 | Moriya et al. | 502/302 |
| 5,883,037 A | 3/1999 | Chopin et al. | 502/308 |
| 5,898,014 A | 4/1999 | Wu et al. | 502/302 |
| 5,905,177 A | 5/1999 | Seo et al. | 570/243 |
| 5,919,727 A | 7/1999 | Brezny | 502/304 |
| 5,922,639 A | 7/1999 | Alario et al. | 502/230 |
| 5,925,590 A | 7/1999 | White et al. | 502/302 |
| 5,935,897 A | 8/1999 | Trubenbach et al. | 502/527.14 |
| 5,935,898 A | 8/1999 | Trubenbach et al. | 502/527.14 |
| 5,945,370 A | 8/1999 | Yokoi et al. | 502/304 |
| 5,945,573 A | 8/1999 | Nappa et al. | 570/175 |
| 5,955,638 A | 9/1999 | Schoebrechts et al. | 570/232 |
| 5,969,195 A | 10/1999 | Stabel et al. | 568/700 |
| 5,972,827 A | 10/1999 | Petit et al. | 502/225 |
| 5,972,830 A | 10/1999 | Yoshida et al. | 502/304 |
| 5,994,260 A | 11/1999 | Bonneau et al. | 502/304 |
| 6,002,019 A | 12/1999 | Tamhankar et al. | 549/285 |
| 6,090,743 A | 7/2000 | Chopin et al. | 502/302 |
| 6,136,048 A | 10/2000 | Birchem et al. | 44/354 |
| 6,165,931 A | 12/2000 | Rao | 502/224 |
| 6,191,329 B1 | 2/2001 | Benje | 570/243 |
| 6,194,345 B1 | 2/2001 | Mangnus et al. | 502/224 |

OTHER PUBLICATIONS

K. Weissermel et al., "Industrial Organic Chemistry," 2$^{nd}$ edition, VCH, Weinheim, pp. 168–175, 1993.

E. T. Lance et al., Preparation, Phase Equilibria, and Crystal Chemistry of Lanthanum, Praseodymium, and Neodymium Hydroxide Chlorides, Journal of Solid State Chemistry, vol. 17, pp. 55–60, 1976.

S. Lin et al., Oxidative Dehydrogenation of Ethane over Lanthanum–Substituted Layered Complex Bismuth Chloride Oxide Catalysts, The Chemical Society of Japan, Chemistry Letters 1997, pp. 901–902.

Pozanski, J., "A Study of the chlorination of lanthanum and neodymium oxides", Materials Science, XVIII, 1992, pp. 99–104.

International Search Report, International application No. PCT/US 00/27700, International filing date: Jun. 10, 2000.

International Search Report, International application No. PCT/US 00/27701, International filing date: Jun. 10, 2000.

International Search Report, International application No. PCT/US 00/27689, international filing date: Jun. 10, 2000.

International Search Report, International application No. PCT/US 00/27272, International filing date: Mar. 10, 2000.

International Search Report, International application No. PCT/US 00/31490, International Filing date: 16/11/2000.

International Search Report, International application No. PCT/US 00/31488, International filing date: 16/11/2000.

"Oxidative Halogenation and Optional Dehydrogenation of C3+ Hydrocarbons", filed in the Unites States on May 23, 2001, U.S. Appl. No. 60/293,132, Applicant: Albert E. Schweizer et al.

Process for vinyl Chloride Manufacture from Ethane and Ethane with Secondary Refractive Consumption of Reactor Effluent HCl:, filed in the United States on May 23, 2001, U.S. Appl. No. 60/292,994, Applicant: William D. Clark et al.

"Production of Vinyl Halide from Single Feedstocks", filed in the United States on May 23, 2001, U.S. Appl. No. 60/292,945, Applicant: William D. Clark et al.

\* cited by examiner

PROCESS FOR THE CONVERSION OF ETHYLENE TO VINYL CHLORIDE AND NOVEL CATALYST COMPOSITIONS USEFUL FOR SUCH PROCESS

CROSS-REFERENCE TO RELATED APPLICATIONS

This application is a 371 of International Patent Application serial number PCT/US00/27272, filed Oct. 3, 2000, which claims the benefit of U.S. provisional patent application Ser. No. 60/166,897, filed Nov. 22, 1999.

Vinyl chloride monomer (VCM) is used extensively as a monomer in the manufacture of polyvinyl chloride (PVC) resins, large volume, versatile plastic materials. This invention disclosed herein relates to a process and catalyst for the catalytic production of VCM from ethylene-containing streams. The process uses a novel catalyst allowing direct production of VCM in a single reactor system. Ethane may also, as a substantial further advantage, be included as a feedstock into this reactor system.

Presently, VCM is most commonly produced from ethylene and chlorine by first chlorinating ethylene to produce 1,2-dichloroethane. The 1,2-dichloroethane is then thermally dehydrochlorinated to yield VCM and a hydrogen chloride (HCl) by-product. The HCl produced in the dehydrochlorination reactor is typically captured and supplied to an oxychlorination reactor. The oxychlorination process catalytically converts ethylene, HCl and oxygen to 1,2-dichloroethane, which is also dehydrochlorinated to yield VCM. Consequently, the above process generally includes three separate reactor sections—a direct chlorination section, an oxychlorination section and a dehydrochlorination section. Plants operated in this manner introduce ethylene, chlorine and oxygen, and produce substantially VCM and water. The complexity of the three reactor sections has led to a search for methods to produce VCM directly from hydrocarbon feedstocks in a single reactor section.

Further, ethylene is a capital-intensive material to produce, and the cost of ethylene generally is a significant factor in the total cost of producing VCM according to the above-described process. Precisely because of this last-described disadvantage of the conventional balanced technology, it has also long been sought to commercialize a process for producing VCM from ethane as a starting material.

A further disadvantage of the prior art for direct production of VCM common to both the ethane- and ethylene-based processes pertains to a less than desirable selectivity to VCM (often being less than 30 percent). This less than desirable selectivity to VCM is largely attributable to formation of byproducts during the oxychlorination reaction. Most of the by-products either derive from combustion products which are generated by oxidation of hydrocarbons such as ethane to form, mainly, CO and $CO_2$ (the combination of which will be referred to as $CO_x$), or the by-products are various chlorinated hydrocarbon derivatives (commonly, ethyl chloride, 1, 1-dichloroethane, 1,2-dichloroethane, 1,1,2-trichloroethane, 1,1-dichloroethylene, cis-1,2-dichloroethylene, trans-1,2-dichloroethylene, trichloroethylene, and perchloroethylene). Formation of tri-, tetra-, penta- and hexachlorinated species is particularly undesirable due to their toxicity and physical properties. Prior art has proposed handling these byproducts primarily by means of either vent and disposal or by selectively separating and recycling some of the chlorinated by-products back to the oxychlorination reactor. Typically, the recycling requires numerous purification and conversion steps prior to utilizing the recycled products in the oxychlorination reactor. For example, the unsaturated chlorinated hydrocarbons are typically converted to saturated forms by a hydrogenation step.

The present invention lacks the disadvantages present in known VCM manufacturing methods as described above. In a first aspect of the present invention, there is provided a simplified VCM process, as compared to the "Balanced VCM Process", in which VCM can be made from ethylene, from ethane and ethylene or essentially from ethane with the recycle of ethylene from the product stream. The process for producing vinyl chloride according to this first aspect includes the essential steps of: (a) combining reactants including ethylene, an oxygen source, and a chlorine source in a reactor containing a catalyst under conditions sufficient to produce a product stream comprising vinyl chloride, ethylene and hydrogen chloride; and (b) recycling ethylene in the product stream back for use in Step (a). The ethylene in question for Step (a) can be accompanied by ethane as a further hydrocarbon starting material, and can be comprised solely of recycled ethylene from the product stream, so that ethane in effect is alone used over time as the requisite $C_2$ hydrocarbon feed. The catalyst utilized for this process in preferred embodiments may be characterized as a porous rare earth element-containing material (a "rare earth material"), with the proviso in this particular embodiment that the catalyst is substantially free of iron and copper and with the further proviso that when cerium is present the catalyst further comprises at least one more rare earth other than cerium.

In a second related aspect of the present invention, there is provided a composition of matter that is useful as a catalyst for the aforementioned process. The composition is of the formula MOCl, wherein M is at least one rare earth element chosen from lanthanum, cerium, neodymium, praseodymium, dysprosium, samarium, yttrium, gadolinium, erbium, ytterbium, holmium, terbium, europium, thulium, lutetium, or mixtures thereof, with the proviso that, when cerium is present, at least one more rare earth element other than cerium is also present. A method for forming this composition comprises the following steps: (a) preparing a solution of a chloride salt of the rare earth element or elements in a solvent comprising either water, an alcohol, or mixtures thereof; (b) adding a nitrogen-containing base to cause the formation of a precipitate; and (c) collecting, drying and calcining the precipitate in order to form the MOCl composition.

In a third related aspect of the present invention, an additional composition of matter is provided which is useful as a catalyst for the aforementioned process. The composition is of the formula $MCl_3$, wherein M is at least one rare earth element from lanthanum, cerium, neodymium, praseodymium, dysprosium, samarium, yttrium, gadolinium, erbium, ytterbium, holmium, terbium, europium, thulium, lutetium, or mixtures thereof, with the proviso that, when cerium is present, at least one more rare earth element other than cerium is also present. A method for forming this composition comprises the following steps: (a) preparing a solution of a chloride salt of the rare earth element or elements in a solvent comprising either water, an alcohol, or mixtures thereof; (b) adding a nitrogen-containing base to cause the formation of a precipitate; (c) collecting, drying and calcining the precipitate; and (d) contacting the calcined precipitate with a chlorine source.

As mentioned, a key distinguishing feature of the process of the present invention lies in the recycling of ethylene from the product stream back to the reactor for carrying out the first step. Preferably, after drying according to methods known in the art, the hydrogen chloride produced in the product stream is also then recycled back for use in the first step. Carbon monoxide present in the product stream may also be recycled back to the first step of the process.

In contrast to the known processes, high VCM selectivity can be produced by the process of the present invention from an ethylene-containing feed, by using catalysts of the character described herein. Typically, VCM selectivity for the process is greater than 50 percent, based on $C_2$ converted. $C_2$ refers to ethylene fed to the reactor system as the sole hydrocarbon source or in combination with ethane. Preferably, VCM selectivity is greater than 60 percent, based on $C_2$ converted. More preferably, VCM selectivity is greater than 65 percent, based on $C_2$ converted, and most preferably, VCM selectivity for the process is greater than 70 percent, based on $C_2$ converted. One reason for the higher VCM selectivities is due to the fact that, at typical temperatures of operation for the process (which are generally lower than disclosed in comparative prior art processes for making VCM), the catalysts disclosed herein enable significantly reduced levels of the undesirable higher chlorinated species such as the tri-, tetra-, penta- and hexachlorinated species.

An additional advantage of this process is that it may employ ethane with the ethylene as a hydrocarbon source. Preferably, much of the ethane is oxidatively dehydrogenated to ethylene in the reactor. The catalyst and process of the present invention allow the recycle of part or all of the ethylene from the product stream directly back to the reactant stream. Any unreacted ethane present in the product stream can advantageously also be recycled back to the first step of the process. Optionally, other light gases, such as the products of combustion, can be contained in the recycled stream. When utilizing a co-feed of ethane, the process is preferably operated with an ethylene balance such that the total moles per minute (that is, "flux") of ethylene in the product stream is substantially equal to the total moles per minute of ethylene entering the reactor. In effect, the ethylene has the appearance of being continuously recycled without depletion while the ethane is substantially consumed in the reactor. A preferred mode of practicing the invention is thus for the recycle stream to become the sole source of ethylene for the first step and for ethane to provide the source of new $C_2$ hydrocarbon into the process.

The preferred chlorine and oxygen sources are gases. The most preferred oxygen source is oxygen. Desirable chlorine sources comprise hydrogen chloride, chlorine, chlorinated hydrocarbons containing labile chlorines, and mixtures thereof. Preferred chlorine sources which are considered "chlorinated hydrocarbons containing labile chlorines" include carbon tetrachloride, 1,2-dichloroethane, ethyl chloride, and mixtures thereof. Most preferably, at least some measure of chlorine gas ($Cl_2$) is continuously present in the reactant stream. It has been determined in this regard that when $Cl_2$ is employed in the reactant stream as a chlorine source, for any given set of conditions the amount of combustion products ($CO_x$) can be reduced compared to where $Cl_2$ is not so used. Alternatively, where another chlorine source, for example, hydrogen chloride (including hydrogen chloride recovered from the product stream and recycled), is contemplated to be used as the sole chlorine source in normal operations, then $Cl_2$ will be supplied to the catalyst both initially and after an interruption in the process before bringing the process fully back on-line, on the additional finding that after treatment (or pretreatment) with $Cl_2$ the catalyst's tendency to make these products of combustion can be reduced substantially, compared to the circumstance wherein $Cl_2$ has not been used to treat or condition the catalyst.

In light of the disclosure herein, those of skill in the art are capable of varying conditions in the reactor in order for the conditions to be sufficient for producing a product stream comprising vinyl chloride, ethylene, and hydrogen chloride. Conditions which are typically varied by those skilled in the art include: the molar feed ratios of the reactants; temperature; pressure; and space time. Preferably, the reactor is maintained between a temperature of greater than 350 degrees Celsius, more preferably greater than 375 degrees Celsius and a temperature less than 500 degrees Celsius, more preferably less than 450 degrees Celsius. Typically, the reactor is maintained between ambient pressure and 3.5 megapascals (MPa), gauge (500 pounds per square inch, gauge (psig)). Operation at pressure allows considerable flexibility to the down-stream processing operations, since higher pressure provides a driving force for the movement of materials into and through separation unit operations. Preferably, the operating pressure is between ambient and 2.1 MPa, gauge (300 psig), and most preferably between ambient and 1.1 MPa, gauge (150 psig). The process can be carried out in either a fixed bed or fluidized bed mode, though a fluidized process is preferred.

Another aspect pertains to the catalyst utilized for the process of this invention. While the aforementioned process is the primary focus for the catalyst that is herein disclosed, the catalyst does have additional utilities, for example, as a catalyst precursor, as a regenerable absorbent, as a catalyst support, and as a catalyst for other processes. As illustrative, rare earth oxychlorides can be used as regenerable bases by exposing them to HCl, wherein they are converted to their respective rare earth chlorides, liberating water. Exposure of rare earth chlorides to water result in conversion back to rare earth oxychlorides, liberating HCl. It is noteworthy that particles and pellets of rare earth oxychlorides do not undergo gross changes in shape or dimension upon chlorination. In contrast, pure oxides of the rare earths can undergo gross changes upon chlorination which cause severe fracturing of prepared particles. Rare earth chlorides also react with methanol to yield methyl chloride. Therefore, the catalyst can be used in catalytic processes for production of methyl chloride free of HCl.

The catalyst can also be useful for ethane dehydrogenation since contacting a stream of ethane, oxygen and a chlorine source such as HCl with the catalyst results in the production of a stream comprising predominantly ethylene and HCl. In addition, contacting the catalyst with a stream containing one or more of ethyl chloride, 1,2-dichloroethane and 1,1,2-trichloroethane results in the hydrodechlorination of these materials to yield HCl and a respective, corresponding unsaturated hydrocarbon or chlorohydrocarbon. Furthermore, when copper salts are contacted with the catalyst (either by their presence in solution during the precipitation or by introduction of copper containing solutions to the calcined catalyst), treating the catalyst with HCl yields a catalyst which is useful for the oxychlorination of ethylene to 1,2-dichloroethane. The catalysts are particularly desirable due to their ability to run at higher temperatures without increased production of COX.

As described previously, the catalyst of this invention comprises at least one rare earth material. The rare earths are a group of 17 elements consisting of scandium (atomic number 21), yttrium (atomic number 39) and the lanthanides (atomic numbers 57–71) [James B. Hedrick, U.S. Geological Survey—Minerals Information—1997, "Rare-Earth Metals"]. The catalyst can be provided as either a porous, bulk material or it can be supported on a suitable support. Preferred rare earth materials are those based on lanthanum, cerium, neodymium, praseodymium, dysprosium, samarium, yttrium, gadolinium, erbium, ytterbium, holmium, terbium, europium, thulium, and lutetium. Most preferred rare earth materials for use in the aforementioned VCM process are based on those rare earth elements which are typically considered as being single valency materials. Catalytic performance of multi-valency materials appears to be less desirable than those that are single valency. For example, cerium is known to be an oxidation-reduction catalyst having the ability to access both the 3+ and 4+stable oxidation states. This is one reason why, if the rare earth material is based on cerium, the catalyst of this invention further comprises at least one more rare earth element other than cerium. Preferably, if one of the rare earths employed in the catalyst is cerium, the cerium is provided in a molar ratio that is less than the total amount of other rare earths present in the catalyst. More preferably, however, substantially no cerium is present in the catalyst. By "substantially no cerium" it is meant that any cerium is in an amount less than 33 atom percent of the rare earth components, preferably less than 20 atom percent, and most preferably less than 10 atom percent.

The rare earth material for the catalyst of this invention is more preferably based upon lanthanum, neodymium, praseodymium or mixtures of these. Most preferably, at least one of the rare earths used in the catalyst is lanthanum. Furthermore, for the ethylene-containing feed to VCM process of this invention, the catalyst is substantially free of iron and copper. In general, the presence of materials that are capable of oxidation-reduction (redox) is undesirable for the catalyst. It is preferable for the catalyst to also be substantially free of other transition metals that have more than one stable oxidation state. For example, manganese is another transition metal that is preferably excluded from the catalyst. By "substantially free" it is meant that the atom ratio of rare earth element to redox metal in the catalyst is greater than 1, preferably greater than 10, more preferably greater than 15, and most preferably greater than 50.

As stated above, the catalyst may also be deposited on an inert support. Preferred inert supports include alumina, silica gel, silica-alumina, silica-magnesia, bauxite, magnesia, silicon carbide, titanium oxide, zirconium oxide, zirconium silicate, and combinations thereof. However, in a most preferred embodiment, the support is not a zeolite. When an inert support is utilized, the rare earth material component of the catalyst typically comprises from 3 weight percent (wt percent) to 85 wt percent of the total weight of the catalyst and support. The catalyst may be supported on the support using methods already known in the art.

It may also be advantageous to include other elements within the catalyst in both of the porous, bulk material and supported forms. For example, preferable elemental additives include alkaline earths, boron, phosphorous, sulfur, silicon, germanium, titanium, zirconium, hafnium, aluminum, and combinations thereof. These elements can be present to alter the catalytic performance of the composition or to improve the mechanical properties (for example attrition-resistance) of the material.

Prior to combining the ethylene-containing feed, oxygen source, and chlorine source in the reactor for the VCM process embodiment of this invention, it is preferable for the catalyst composition to comprise a salt of at least one rare earth element with the proviso that the catalyst is substantially free of iron and copper and with the further proviso that when cerium is employed the catalyst further comprises at least one more rare earth element other than cerium. The salt of at least one rare earth element is preferably selected from rare earth oxychlorides, rare earth chlorides, rare earth oxides, and combinations thereof, with the proviso that the catalyst is substantially free of iron and copper and with the further proviso that when cerium is used the catalyst further comprises at least one more rare earth element other than cerium. More preferably, the salt comprises a rare earth oxychloride of the formula MOCl, wherein M is at least one rare earth element chosen from lanthanum, cerium, neodymium, praseodymium, dysprosium, samarium, yttrium, gadolinium, erbium, ytterbium, holmium, terbium, europium, thulium, lutetium, or mixtures thereof, with the proviso that, when cerium is present, at least one more rare earth element other than cerium is also present. Most preferably, the salt is a porous, bulk lanthanum oxychloride (LaOCl) material. As has been mentioned, this material beneficially does not undergo gross changes (for example, fracturing) when chlorinated in situ in this process, and provides the further beneficial property of water solubility in the context of this process after a period of use (LaOCl is initially water-insoluble), so that should spent catalyst need to be removed from a fluidized bed, fixed bed reactor or other process equipment or vessels, this can be done without hydroblasting or conventional labor-intensive mechanical techniques by simply flushing the spent catalyst from the reactor in question with water.

Typically, when the salt is a rare earth oxychloride (MOCl), it has a BET surface area of at least 12 $m^2/g$, preferably at least 35 $m^2/g$, more preferably at least 20 $m^2/g$, and most preferably at least 30 $m^2/g$. Generally, the BET surface area is less than 200 $m^2/g$. For these above measurements, the nitrogen adsorption isotherm was measured at 77K and the surface area was calculated from the isotherm data utilizing the BET method (Brunauer, S., Emmett, P. H., and Teller, E., J. Am. Chem. Soc., 60, 309 (1938)). In addition, it is noted that the MOCl phases possess characteristic powder X-Ray Diffraction (XRD) patterns that are distinct from the $MCl_3$ phases.

It is also possible, as indicated in several instances previously, to have mixtures of the rare earths ("M") within the MOCl composition. For example, M can be a mixture of at least two rare earths selected from lanthanum, cerium, neodymium, praseodymium, dysprosium, samarium, yttrium, gadolinium, erbium, ytterbium, holmium, terbium, europium, thulium and lutetium. Similarly, it is also possible to have mixtures of different MOCl compositions wherein M is different as between each composition of the MOCl's in the mixture.

Once the ethylene-containing feed, oxygen source, and chlorine source are combined in the reactor, a catalyst is formed in situ from the salt of at least one rare earth element.

Although this characterization should not limit the composition or process of this invention in any way, it is believed that the in situ formed catalyst comprises a chloride of the rare earth component. An example of such a chloride is $MCl_3$, wherein M is a rare earth component selected from lanthanum, cerium, neodymium, praseodymium, dysprosium, samarium, yttrium, gadolinium, erbium, ytterbium, holmium, terbium, europium, thulium, lutetium and mixtures thereof, with the proviso that when cerium is present the catalyst further comprises at least one more rare earth element other than cerium. Typically, when the salt is a rare earth chloride ($MCl_3$), it has a BET surface area of at least 5 $m^2/g$, preferably at least 10 $m^2/g$, more preferably at least 15 $m^2/g$, more preferably at least 20 $m^2/g$, and most preferably at least 30 $m^2/g$.

Oxychlorination is conventionally referenced as the oxidative addition of two chlorine atoms to ethylene from HCl or other reduced chlorine source. Catalysts capable of performing this chemistry have been classified as modified Deacon catalysts [Olah, G. A., Molnar, A., Hydrocarbon Chemistry, John Wiley & Sons (New York, 1995), pg 226]. Deacon chemistry refers to the Deacon reaction, the oxidation of HCl to yield elemental chlorine and water.

Without being limiting of the present invention as claimed hereafter, in contrast to oxychlorination, the preferred process and catalyst described above are considered as utilizing oxydehydro-chlorination in converting ethane-containing and ethylene-containing streams to VCM at high selectivity. Oxydehydro-chlorination is the conversion of a hydrocarbon (using oxygen and a chlorine source) to a chlorinated hydrocarbon wherein the carbons either maintain their initial valence or have their valency reduced (i.e., $sp^3$ carbons remain $sp^3$ or are converted to $sp^2$, and $sp^2$ carbons remain $sp^2$ or are converted to sp). This differs from the conventional definition of oxychlorination, whereby ethylene is convened to 1,2-dichloroethane with a net increase in carbon valency (i.e., $sp^2$ carbons are converted to $sp^3$ carbons).

In light of the disclosure herein, those of skill in the art will undoubtedly recognize alternative methods for preparing the compositions of this invention. A method currently felt to be preferable, however, for forming the composition comprising the rare earth oxychloride (MOCl) comprises the following steps: (a) preparing a solution of a chloride salt of the rare earth element or elements in a solvent comprising either water, an alcohol, or mixtures thereof; (b) adding a nitrogen-containing base to cause the formation of a precipitate; and (c) collecting, drying and calcining the precipitate in order to form the MOCl material. Typically, the nitrogen-containing base is selected from ammonium hydroxide, alkyl amine, aryl amine, arylalkyl amine, alkyl ammonium hydroxide, aryl ammonium hydroxide, arylalkyl ammonium hydroxide, and mixtures thereof. The nitrogen-containing base may also be provided as a mixture of a nitrogen-containing base with other bases that do not contain nitrogen. Preferably, the nitrogen-containing base is tetraalkyl ammonium hydroxide. The solvent in Step (a) is preferably water. Drying of the catalytically-useful composition can be done in any manner, including by spray drying, drying in a purged oven and other known methods. For the presently-preferred fluidized bed mode of operation, a spray-dried catalyst is preferred.

A method currently felt to be preferable for forming the catalyst composition comprising the rare earth chloride ($MCl_3$) comprises the following steps: (a) preparing a solution of a chloride salt of the rare earth element or elements in a solvent comprising either water, an alcohol, or mixtures thereof; (b) adding a nitrogen-containing base to cause the formation of a precipitate; (c) collecting, drying and calcining the precipitate: and (d) contacting the calcined precipitate with a chlorine source. For example, one application of this method (using La to illustrate) would be to precipitate $LaCl_3$ solution with a nitrogen containing base, dry it, add it to the reactor, heat it to 400° C. in the reactor to perform the calcination, and then contact the calcined precipitate with a chlorine source to form the catalyst composition in situ in the reactor.

EXAMPLES

The invention will be further clarified by a consideration of the following examples, which are intended to be purely exemplary.

Example 1

To demonstrate the production of vinyl chloride from a stream comprising ethylene, a porous, refractory composition comprising lanthanum was prepared. A solution of $LaCl_3$ in water was prepared by dissolving one part of commercially available hydrated lanthanum chloride (obtained from J. T. Baker Chemical Company) in 8 parts of deionized water. Dropwise addition with stirring of ammonium hydroxide (obtained from Fisher Scientific, certified ACS specification) to neutral pH (by universal test paper) caused the formation of a gel. The mixture was centrifuged, and the solution decanted away from the solid. Approximately 150 ml of deionized water was added and the gel was stirred vigorously to disperse the solid. The resulting solution was centrifuged and the solution decanted away. This washing step was repeated two additional times. The collected, washed gel was dried for two hours at 120 degrees Celsius and subsequently calcined at 550 deg. C. for four hours in air. The resulting solid was crushed and sieved to yield particles suitable for additional testing. This procedure produced a solid matching the X-ray powder diffraction pattern of LaOCl.

The particles were placed in a pure nickel (alloy 200) reactor. The reactor was configured such that ethylene, ethane, HCl, $O_2$ and inert gas (He and Ar mixture) could be fed to the reactor. The function of the argon was as an internal standard for the analysis of the reactor feed and effluent by gas chromatography. Space time is calculated as the volume of catalyst divided by the flow rate at standard conditions. Feed rates are molar ratios. The reactor system was immediately fed an ethane-containing stream with the stoichiometry of one ethane, one HCl and one oxygen. This provides balanced stoichiometry for the production of VCM from ethylene.

Table 1 below sets forth the results of reactor testing using this composition.

Column 1 of Table 1 shows the high selectivity to vinyl chloride when the catalyst system is fed ethylene under oxidizing conditions in the presence of HCl. The composition contains helium in order to mimic a reactor operated with air as the oxidant gas.

Column 2 of Table 1 shows the high selectivity to vinyl chloride when the catalyst system is fed ethylene under oxidizing conditions in the presence of HCl. The composition is now fuel rich to avoid limitations imposed by flammability and contains no helium.

Column 3 of Table 1 shows the high selectivity to vinyl chloride and ethylene when the catalyst system is fed ethane under oxidizing conditions in the presence of HCl. The composition mimics a reactor operated with air as the oxidant gas. There is no ethylene present in the feed. The ethylene present in the reactor is the product of the partial oxidation of ethane.

Column 4 of Table 1 shows the result when both ethane and ethylene are fed. The reactor is operated in such a way as to insure that the amount of ethylene entering the reactor and exiting the reactor are equal. Operated in this fashion, the ethylene gives the appearance of an inert diluent, and only ethane is being converted. The results show a high yield of vinyl chloride and 1,2-dichloroethane. Argon is used as an internal standard to insure that the ethylene flux entering the reactor and the ethylene flux exiting the reactor are equal. The ratio of the ethylene to argon integrated chromatographic peak is identical for the reactor feed and product stream. In this way the recycle of ethylene is simulated within the reactor device.

TABLE 1

| | Feed Mole Ratios | | | |
|---|---|---|---|---|
| $C_2H_4$ | 2 | 3.7 | 0 | 3 |
| $C_2H_6$ | 0 | 0 | 1 | 2 |
| HCl | 2 | 2 | 1 | 2.5 |
| $O_2$ | 1 | 1 | 1 | 1 |
| Inerts | 6.8 | 0 | 4 | 0 |
| T (deg. C) | 401 | 400 | 401 | 419 |
| Space time (s) | 12.3 | 5.0 | 21.8 | 12.4 |
| $O_2$ conv. (pct) | 47.3 | 53.7 | 54.8 | 93.9 |
| | Selectivities (Percent) | | | |
| $C_2H_4$ | — | — | 44.7 | — |
| $C_2H_4Cl_2$ | 10.7 | 14.0 | 0.1 | 12.8 |
| VCM | 76.6 | 78.1 | 34.5 | 68.5 |

Example 2

To further demonstrate the utility of the composition, ethylene is oxidatively converted to vinyl chloride using a variety of chlorine sources. A solution of $LaCl_3$ in water was prepared by dissolving one part of commercially available hydrated lanthanum chloride (purchased from Avocado Research Chemicals Ltd.) in 6.6 parts of deionized water. Rapid addition with stirring of 6 M ammonium hydroxide in water-(diluted certified ACS reagent, obtained from Fisher Scientific) caused the formation of a gel. The mixture was filtered to collect the solid. The collected gel was dried at 120 deg C. prior to calcination at 550 deg C. for four hours in air. The resulting solid was crushed and sieved. The sieved particles were placed in a pure nickel (alloy 200) reactor. The reactor was configured such that ethylene, HCl, oxygen, 1,2-dichloroethane, carbon tetrachloride and helium could be fed to the reactor. Space time is calculated as the volume of catalyst divided by the flow rate at standard temperature and pressure. Feed rates are molar ratios. The composition was heated to 400 deg C. and treated with a 1:1:3 $HCl:O_2$:He mixture for 2 hours prior to the start of operation.

The composition formed was operated to produce vinyl chloride by feeding ethylene, a chlorine source and oxygen at 400 deg C. The following table shows data obtained between 82 and 163 hours on stream using different chlorine sources. Chlorine is supplied as HCl, carbon tetrachloride and 1,2-dichloroethane. VCM signifies vinyl chloride. Space time is calculated as the volume of catalyst divided by the flow rate at standard temperature and pressure. The reactors are operated with the reactor exit at ambient pressure. Both ethylene and 1,2-dichloroethane are termed to be $C_2$ species.

TABLE 2

| | Feed mole ratios | | | |
|---|---|---|---|---|
| $C_2H_4$ | 2.0 | 2.0 | 2.0 | 2.0 |
| $C_2H_6$ | 0.0 | 0.0 | 0.0 | 0.0 |
| $CCl_4$ | 0.5 | 0.5 | 0.0 | 0.0 |
| $C_2H_4Cl_2$ | 0.0 | 0.0 | 1.8 | 0.0 |
| HCl | 0.0 | 0.0 | 0.0 | 1.9 |
| $O_2$ | 1.0 | 1.0 | 1.0 | 1.0 |
| He + Ar | 8.9 | 9.0 | 8.9 | 6.7 |
| T (deg C) | 400 | 399 | 401 | 400 |
| Space time (s) | 8.0 | 4.0 | 8.6 | 4.9 |
| | Fractional conversions (Percent) | | | |
| $C_2H_4$ | 40.4 | 27.0 | 18.7 | 20.1 |
| $C_2H_6$ | 0.0 | 0.0 | 0.0 | 0.0 |
| $CCl_4$ | 94.8 | 78.4 | 0.0 | 0.0 |
| $C_2H_4Cl_2$ | 0.0 | 0.0 | 98.3 | 0.0 |
| HCl | 0.0 | 0.0 | 0.0 | 44.7 |
| $O_2$ | 68.8 | 42.0 | 55.2 | 37.8 |
| | Selectivities based on moles of $C_2$ converted | | | |
| VCM | 59.6 | 56.4 | 86.0 | 78.5 |
| $C_2H_4Cl_2$ | 14.8 | 30.7 | 0.0 | 2.2 |
| $C_2H_5Cl$ | 0.6 | 0.4 | 0.2 | 1.6 |

These data show that a variety of chlorine sources can be used in the oxidative production of vinyl. The use of carbon tetrachloride, 1,2-dichloroethane and HCl all produce vinyl chloride as the dominant product.

Example 3

A solution of $LaCl_3$ in water was prepared by dissolving one part of commercially available hydrated lanthanum chloride (purchased from Avocado Research Chemicals Ltd.) in 6.67 parts of deionized water. Rapid addition with stirring of 6 M ammonium hydroxide in water (diluted certified ACS reagent, obtained from Fisher Scientific) caused the formation of a gel and yielded a final pH of 8.85. The mixture was filtered to collect the solid. The collected material was calcined in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor.

Table 3 shows data wherein the reactor feeds were adjusted such that the flux of ethylene (moles/minute) entering the reactor and the flux of ethylene exiting the reactor were substantially equal. Reactor feeds were similarly adjusted such that the fluxes of HCl entering and exiting the reactor were substantially equal. Oxygen conversion was set at slightly less than complete conversion to enable the monitoring of catalyst activity. Operated in this manner, the consumed feeds are ethane, oxygen, and chlorine. Both ethylene and HCl give the appearance of neither being created nor consumed. Space time is calculated as the volume of catalyst divided by the flow rate at standard temperature and pressure. The example further illustrates the use of chlorine gas as a chlorine source in the production of vinyl chloride.

TABLE 3

| Feed mole ratios | |
|---|---|
| $C_2H_4$ | 21 |
| $C_2H_6$ | 4.5 |
| $Cl_2$ | 0.5 |
| HCl | 2.4 |
| $O_2$ | 1.0 |
| He + Ar | 7.4 |
| T (° C.) | 400 |
| Space time (s) | 9.4 |
| Fractional conversions (Pct.) | |
| $C_2H_4$ | 1.8 |
| $C_2H_6$ | 27.3 |
| $Cl_2$ | 99.8 |
| HCl | −1.4 |
| $O_2$ | 96.4 |
| Selectivities (Pct) | |
| VCM | 79.0 |
| $C_2H_4Cl_2$ | 7.2 |
| $C_2H_5Cl$ | 1.7 |

TABLE 3-continued

| | |
|---|---|
| $CO_x$ | 5.1 |
| $C_2H_4$ | 0.5 |

In common with all examples herein, VCM signifies vinyl chloride. $C_2H_4Cl_2$ is solely 1,2-dichloroethane. $CO_x$ is the combination of CO and $CO_2$.

Example 4

The catalyst composition prepared in Example 1 was operated to show the effect of temperature on catalyst performance. The results are shown in Table 4.

TABLE 4

Temperature Effects on Lanthanum Composition

| Feed mole ratios | | | |
|---|---|---|---|
| $C_2H_4$ | 1.9 | 1.9 | 1.9 |
| $C_2H_6$ | 0.0 | 0.0 | 0.0 |
| $Cl_2$ | 0.0 | 0.0 | 0.0 |
| HCl | 1.9 | 1.9 | 1.5 |
| $O_2$ | 1.0 | 1.0 | 1.0 |
| He + Ar | 6.6 | 6.6 | 7.1 |
| T (° C.) | 349 | 399 | 450 |
| Space time (s) | 4.9 | 9.7 | 9.6 |
| Fractional conversions (Pct) | | | |
| $C_2H_4$ | 8.2 | 33.0 | 35.2 |
| $C_2H_6$ | 0.0 | 0.0 | 0.0 |
| $Cl_2$ | | | |
| HCl | 7.5 | 36.0 | 46.5 |
| $O_2$ | 8.8 | 49.2 | 57.1 |
| Selectivities (Pct) | | | |
| VCM | 67.7 | 87.4 | 79.8 |
| $C_2H_4Cl_2$ | 2.5 | 0.2 | 0.8 |
| $C_2H_5Cl$ | 28.1 | 1.3 | 0.4 |
| $CO_x$ | 1.6 | 0.9 | 8.9 |

These data show that the ability of the composition to produce vinyl chloride is little changed by increasing temperature. Lower temperature decreases rates but selectivity is only altered in a minor way.

Example 5 Through Example 12

Example 5 through Example 12 illustrate the preparation of numerous rare earth compositions, each containing only one rare earth material. Data illustrating the performance of these compositions are set forth in Table 5.

Example 5

A solution of $LaCl_3$ in water was prepared by dissolving one part of commercially available hydrated lanthanum chloride (purchased from Aldrich Chemical Company) in 6.67 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The gel was resuspended in 6.66 parts of deionized water. Centrifuging allowed collection of the gel. The collected gel was dried at 120 deg C. prior to calcination at 550 deg C. for four hours in air. The resulting solid was crushed and sieved. The sieved particles were placed in a pure nickel (alloy 200) reactor. The reactor was configured such that ethylene, ethane. HCl, oxygen, and inert (helium and argon mixture) could be fed to the reactor. Powder x-ray diffraction shows the material to be LaOCl. The BET surface area is measured to be 42.06 $m^2/g$. The specific performance data for this example are set forth below in Table 5.

Example 6

A solution of $NdCl_3$ in water was prepared by dissolving one part of commercially available hydrated neodymium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. Powder x-ray diffraction shows the material to be NdOCl. The BET surface area is measured to be 22.71 $m^2/g$. The specific performance data for this example are set forth below in Table 5.

Example 7

A solution of $PrCl_3$ in water was prepared by dissolving one part of commercially available hydrated praseodymium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. Powder x-ray diffraction shows the material to be PrOCl. The BET surface area is measured to be 21.37 $m^2/g$. The specific performance data for this example are set forth below in Table 5.

Example 8

A solution of $SmCl_3$ in water was prepared by dissolving one part of commercially available hydrated samarium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. Powder x-ray diffraction shows the material to be SmOCl. The BET surface area is measured to be 30.09 $m^2/g$. The specific performance data for this example are set forth below in Table 5.

Example 9

A solution of $HoCl_3$ in water was prepared by dissolving one part of commercially available hydrated holmium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 20.92 $m^2/g$. The specific performance data for this example are set forth below in Table 5.

Example 10

A solution of $ErCl_3$ in water was prepared by dissolving one part of commercially available hydrated erbium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 19.80 $m^2/g$. The specific performance data for this example are set forth below in Table 5.

Example 11

A solution of $YbCl_3$ in water was prepared by dissolving one part of commercially available hydrated ytterbium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 2.23 $m^2/g$. The specific performance data for this example are set forth below in Table 5.

Example 12

A solution of $YCl_3$ in water was prepared by dissolving one part of commercially available hydrated yttrium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 29.72 $m^2/g$. The specific performance data for this example are set forth below in Table 5.

TABLE 5

Rare Earth Oxychloride Compositions Operated to Produce Vinyl Chloride

| Example | 5 | 6 | 7 | 8 | 9 | 10 | 11 | 12 |
|---|---|---|---|---|---|---|---|---|
| Feed mole ratios | | | | | | | | |
| $C_2H_4$ | 3.6 | 4.2 | 3.7 | 3.6 | 3.6 | 3.6 | 4.2 | 3.6 |
| HCl | 2.0 | 2.3 | 2.0 | 2.0 | 2.0 | 2.0 | 2.3 | 2.0 |
| $O_2$ | 1.0 | 1.0 | 1.0 | 1.0 | 1.0 | 1.0 | 1.0 | 1.0 |
| He + Ar | 0.2 | 0.2 | 0.2 | 0.2 | 0.2 | 0.2 | 0.2 | 0.2 |
| T (deg C.) | 399 | 403 | 401 | 400 | 400 | 400 | 400 | 399 |
| Space time (s) | 8.7 | 21.3 | 11.4 | 17.6 | 17.7 | 22.8 | 23.1 | 21.3 |
| Fractional conversions (Percent) | | | | | | | | |
| $C_2H_4$ | 23.7 | 13.2 | 22.8 | 14.7 | 12.7 | 15.4 | 3.3 | 13.8 |
| HCl | 47.6 | 24.9 | 40.9 | 20.8 | 15.9 | 22.4 | 5.0 | 19.8 |
| $O_2$ | 58.8 | 59.4 | 55.0 | 53.4 | 48.1 | 48.8 | 21.2 | 47.8 |
| Selectivities (Percent) | | | | | | | | |
| VCM | 75.3 | 74.4 | 74.2 | 61.0 | 33.3 | 44.0 | 6.1 | 35.0 |
| $C_2H_4Cl_2$ | 11.3 | 2.9 | 6.1 | 2.9 | 14.5 | 17.5 | 8.8 | 18.8 |
| $C_2H_5Cl$ | 3.5 | 6.9 | 4.4 | 10.6 | 16.8 | 12.8 | 37.0 | 16.5 |
| $CO_x$ | 4.8 | 11.8 | 9.7 | 22.4 | 33.8 | 23.1 | 26.4 | 27.5 |

These data show the utility of bulk rare earth containing compositions for the conversion of ethylene containing streams to vinyl chloride.

Example 13 Through Example 17

Example 13 through Example 17 illustrate the preparation of numerous rare earth compositions, each containing a mixture of rare earth materials. Data illustrating the performance of these data are set forth in Table 6.

Example 13

A solution of $LaCl_3$ and $NdCl_3$ in water was prepared by dissolving one part of commercially available hydrated lanthanum chloride (purchased from Spectrum Quality Products) and 0.67 parts of commercially available hydrated neodymium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.96. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 21.40 $m^2/g$. The specific performance data for this example are set forth below in Table 6.

Example 14

A solution of $LaCl_3$ and $SmCl_3$ in water was prepared by dissolving one part of commercially available hydrated lanthanum chloride (purchased from Spectrum Quality Products) and 0.67 parts of commercially available hydrated samarium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.96. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 21.01 m$^2$/g. The specific performance data for this example are set forth below in Table 6.

Example 15

A solution of LaCl$_3$ and YCl$_3$ in water was prepared by dissolving one part of commercially available hydrated lanthanum chloride (purchased from Spectrum Quality Products) and 0.52 parts of commercially available hydrated yttrium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.96. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 20.98 m$^2$/g. The specific performance data for this example are set forth below in Table 6.

Example 16

A solution of LaCl$_1$ and HoCl$_3$ in water was prepared by dissolving one part of commercially available hydrated lanthanum chloride (purchased from Spectrum Quality Products) and one part of commercially available hydrated holmium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.64. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 19.68 m$^2$/g. The specific performance data for this example are set forth below in Table 6.

Example 17

A solution of LaCl$_3$ and HoCl$_3$ in water was prepared by dissolving one part of commercially available hydrated lanthanum chloride (purchased from Spectrum Quality Products) and 0.75 parts of commercially available hydrated ytterbium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 9.10. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 20.98 m$^2$(g. The specific performance data for this example are set forth below in Table 6.

TABLE 6

Performance of Compositions Containing Two Rare earth materials

| Example | 13 | 14 | 15 | 16 | 17 |
|---|---|---|---|---|---|
| Feed mole ratios | | | | | |
| $C_2H_4$ | 3.7 | 3.6 | 3.6 | 3.6 | 3.6 |
| HCl | 2.0 | 2.0 | 2.0 | 2.0 | 2.0 |
| $O_2$ | 1.0 | 1.0 | 1.0 | 1.0 | 1.0 |
| He + Ar | 0.2 | 0.2 | 0.2 | 0.2 | 0.2 |
| T (° C.) | 401 | 401 | 400 | 399 | 400 |
| Space time (s) | 3.7 | 15.7 | 13.7 | 16.9 | 20.6 |
| Fractional conversions (Percent) | | | | | |
| $C_2H_4$ | 16.8% | 11.3 | 12.5 | 12.4 | 9.2 |
| HCl | 36.0 | 13.1 | 18.1 | 11.9 | 15.9 |
| $O_2$ | 45.9 | 47.2 | 52.2 | 47.1 | 38.7 |
| Selectivities (Percent) | | | | | |
| VCM | 75.8 | 51.0 | 51.4 | 28.9 | 11.1 |
| $C_2H_4Cl_2$ | 9.7 | 7.5 | 12.4 | 14.5 | 20.6 |
| $C_2H_5Cl$ | 4.1 | 11.8 | 8.9 | 17.0 | 23.8 |
| $CO_x$ | 6.9 | 27.5 | 25.8 | 38.9 | 43.8 |

These data further show the utility of bulk rare earth containing compositions containing mixtures of the rare earth materials for the conversion of ethylene containing streams to vinyl chloride.

Example 18 Through Example 25

Example 18 through Example 25 are compositions containing rare earth materials with other additives present.

Example 18

A solution of LaCl$_3$ in water was prepared by dissolving one part of commercially available hydrated lanthanum chloride (purchased from Aldrich Chemical Company) in 6.67 parts of deionized water. 0.48 parts of ammonium hydroxide (Fisher Scientific) was added to 0.35 parts of commercially prepared CeO$_2$ powder (Rhone-Poulenc): The lanthanum and cerium containing mixtures were added together with stirring to form a gel. The resulting gel containing mixture was filtered and the collected solid was calcined in air at 550 deg C. for 4 hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The specific performance data for this example are set forth below in Table 7.

Example 19

A lanthanum containing composition prepared using the method of Example 5 was ground with a mortar and pestle to form a fine powder. One part of the ground powder was combined with 0.43 parts BaCl$_2$ powder and further ground using a mortar and pestle to form an intimate mixture. The lanthanum and barium containing mixture was pressed to form chunks. The chunks were calcined at 800 deg C. in air for 4 hours. The resulting material was placed in a pure nickel (alloy 200) reactor. The reactor was configured such that ethylene, ethane, HCl, oxygen, and inert (helium and argon mixture) could be fed to the reactor. The specific performance data for this example are set forth below in Table 7.

Example 20

Dried Grace Davison Grade 57 silica was dried at 120 deg C. for 2 hours. A saturated solution of $LaCl_3$ in water was formed using commercially available hydrated lanthanum chloride. The dried silica was impregnated to the point of incipient wetness with the $LaCl_3$ solution. The impregnated silica was allowed to air dry for 2 days at ambient temperature. It was further dried at 120 deg C. for 1 hour. The resulting material was placed in a pure nickel (alloy 200) reactor. The reactor was configured such that ethylene, ethane, HCl, oxygen, and inert (helium and argon mixture) could be fed to the reactor. The specific performance data for this example are set forth below in Table 7.

Example 21

A solution of $LaCl_3$ in water was prepared by dissolving one part of commercially available hydrated lanthanum chloride (purchased from Spectrum Quality Products) in 6.67 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The gel was resuspended in 12.5 parts of acetone (Fisher Scientific), centrifuged, and the liquid decanted away and discarded. The acetone washing step was repeated 4 additional times using 8.3 parts acetone. The gel was resuspended in 12.5 parts acetone and 1.15 parts of hexamethyldisilizane (purchased from Aldrich Chemical Company) was added and the solution was stirred for one hour. The mixture was centrifuged to collect the gel. The collected gel was allowed to air dry at ambient temperature prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 58.82 $m^2/g$. The specific performance data for this example are set forth below in Table 7.

Example 22

A solution of $LaCl_3$ in water was prepared by dissolving one part of commercially available hydrated lanthanum chloride (Alfa Aesar) and 0.043 parts of commercially available $HfCl_4$ (purchased from Acros Organics) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The collected gel was dried at 80 deg C. overnight prior to calcination at 550 deg C. for 4 hours. The specific performance data for this example are set forth below in Table 7.

Example 23

A solution of $LaCl_3$ in water was prepared by dissolving one part of commercially available hydrated lanthanum chloride (Alfa Aesar) and 0.086 parts of commercially available $HfCl_4$ (purchased from Acros Organics) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded The collected gel was dried at 80 deg C. overnight prior to calcination at 550 deg C. for 4 hours. The specific performance data for this example are set forth below in Table 7.

Example 24

A solution of $LaCl_3$ in water was prepared by dissolving one part of commercially available hydrated lanthanum chloride (Alfa Aesar) and 0.043 parts of commercially available $ZrOCl_2$ (purchased from Acros Organics) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The gel was resuspended in 6.67 parts deionized water and subsequently centrifuged. The solution was decanted away and discarded. The collected gel was calcined at 550 deg C. for 4 hours. The specific performance data for this example are set forth below in Table 7.

Example 25

A solution of $LaCl_3$ in water was prepared by dissolving commercially available hydrated lanthanum chloride in deionized water to yield a 2.16 M solution. Commercially produced zirconium oxide (obtained from Engelhard) was dried at 350 deg C. overnight. One part of the zirconium oxide was impregnated with 0.4 parts of the $LaCl_3$ solution. The sample was dried in air at room temperature and then calcined in air at 550 deg C. for 4 hours. The resulting solid was crushed and sieved. The sieved particles were placed in a pure nickel (alloy 200) reactor. The reactor was configured such that ethylene, ethane, HCl, oxygen, and inert (helium and argon mixture) could beefed to the reactor. The specific performance data for this example are set forth below in Table 7.

TABLE 7

Rare Earth Compositions with Additional Components

| Example | 18 | 19 | 20 | 21 | 22 | 23 | 24 | 25 |
|---|---|---|---|---|---|---|---|---|
| Feed mole ratios | | | | | | | | |
| $C_2H_4$ | 3.7 | 3.6 | 3.7 | 3.7 | 3.7 | 3.7 | 3.6 | 3.7 |
| HCl | 2.0 | 2.0 | 2.0 | 2.0 | 2.0 | 2.0 | 2.0 | 2.0 |
| $O_2$ | 1.0 | 1.0 | 1.0 | 1.0 | 1.0 | 1.0 | 1.0 | 1.0 |
| He + Ar | 0.2 | 0.2 | 0.2 | 0.2 | 0.2 | 0.2 | 0.2 | 0.2 |
| T (° C.) | 400 | 401 | 400 | 399 | 401 | 400 | 400 | 401 |
| Space time (s) | 4.8 | 20.3 | 6.7 | 3.6 | 7.9 | 7.8 | 12.8 | 16.7 |
| Fractional conversions (Percent) | | | | | | | | |
| $C_2H_4$ | 18.2 | 11.7 | 14.1 | 24.6 | 18.5 | 16.5 | 18.7 | 15.2 |
| HCl | 34.6 | 22.1 | 24.4 | 57.1 | 40.9 | 38.2 | 35.2 | 21.1 |
| $O_2$ | 55.6 | 33.2 | 48.0 | 52.0 | 50.3 | 47.4 | 50.9 | 56.4 |
| Selectivities (Percent) | | | | | | | | |
| VCM | 64.5 | 54.6 | 53.6 | 56.0 | 76.4 | 71.8 | 73.2 | 55.1 |
| $C_2H_4Cl_2$ | 11.5 | 15.2 | 10.0 | 31.4 | 9.6 | 12.7 | 5.2 | 7.3 |
| $C_2H_5Cl$ | 5.0 | 10.0 | 7.4 | 2.9 | 4.0 | 4.9 | 4.9 | 12.4 |
| $CO_x$ | 10.8 | 18.6 | 26.6 | 6.0 | 7.6 | 8.8 | 13.6 | 24.1 |

These data show the production of vinyl chloride from ethylene containing streams using lanthanum-based catalysts that contain other elements or are supported.

Example 26 Through Example 31

Example 26 through Example 31 show some of the modifications possible to alter the preparation of useful rare earth compositions.

Example 26

A solution of $LaCl_3$ in water was prepared by dissolving one part of commercially available hydrated lanthanum chloride (purchased from Spectrum Quality Products) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. A saturated solution of 0.61 parts benzyltriethylammonium chloride (purchased from Aldrich Chemical Company) in deionized water was prepared, The solution was added to the gel and stirred. The collected gel was calcined at 550 deg C. for 4 hours. The specific performance data for this example are set forth below in Table 8. This example illustrates the use of added ammonium salts to alter the preparation of rare earth compositions.

Example 27

A solution of $LaCl_3$ in water was prepared by dissolving one part of commercially available hydrated lanthanum chloride (purchased from Spectrum Quality Products) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. One part glacial acetic acid was added to the gel and the gel redissolved. Addition of the solution to 26 parts of acetone caused the formation of a precipitate. The solution was decanted away and the solid was calcined at 550 deg C. for 4 hours. The specific performance data for this example are set forth below in Table 8. This example shows the preparation of useful lanthanum compositions by the decomposition of carboxylic acid adducts of chlorine containing rare earth compounds.

Example 28

A solution of $LaCl_3$ in water was prepared by dissolving one part of commercially available hydrated lanthanum chloride (purchased from Spectrum Quality Products) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. The collected gel was resuspended in 3.33 parts of deionized water. Subsequent addition of 0.0311 parts of phosphoric acid reagent (purchased from Fisher Scientific) produced no visible change in the suspended gel. The mixture was again centrifuged and the solution decanted away from the phosphorus containing gel. The collected gel was calcined for at 550 deg C. for 4 hours. The calcined solid had a BET surface area of 33.05 $m^2/g$. The specific performance data for this example are set forth below in Table 8. This example shows the preparation of a rare earth composition also containing phosphorus, as phosphate.

Example 29

A solution of $LaCl_3$ in water was prepared by dissolving one part of commercially available hydrated lanthanum chloride (purchased from Acros Organics) in 6.66 parts of deionized water. A solution was formed by mixing 0.95 parts of commercially available DABCO, or 1,4-diazabicyclo[2.2.2]octane, (purchased from ICN Pharmaceuticals) dissolved in 2.6 parts of deionized water. Rapid mixing with stirring of the two solutions caused the formation of a gel. The mixture was centrifuged to collect the solid. The collected gel was resuspended in 6.67 parts of deionized water. The mixture was again centrifuged and the solution decanted away from the gel. The collected gel was calcined for 4 hours at 550 deg C. The calcined solid had a BET surface area of 38.77 $m^2/g$. The specific performance data for this example are set forth below in Table 8. This example shows the utility of an alkyl amine in the preparation of a useful rare earth composition.

Example 30

A solution of $LaCl_3$ in water was prepared by dissolving one part of commercially available hydrated lanthanum chloride (purchased from Acros Organics) in 10 parts of deionized water. To this solution, 2.9 parts of commercially available tetramethyl ammonium hydroxide (purchased from Aldrich Chemical Company) was added rapidly and with stirring, causing the formation of a gel. The mixture was centrifuged and the solution decanted away. The collected gel was resuspended in 6.67 parts of deionized water. The mixture was again centrifuged and the solution decanted away from the gel. The collected gel was calcined for 4 hours at 550 deg C. The calcined solid had a BET surface area of 80.35 $m^2/g$. The specific performance data for this example are set forth below in Table 8. This example shows the utility of an alkyl ammonium hydroxide for formation of a useful rare earth composition.

Example 31

A solution of $LaCl_3$ in water was prepared by dissolving one part of commercially available hydrated lanthanum chloride (purchased from Avocado Research Chemicals Ltd.) in 6.67 parts of deionized water. To this solution, 1.63 parts of commercially available 5 N NaOH solution (Fisher Scientific) was added rapidly and with stirring, causing the formation of a gel. The mixture was centrifuged and the solution decanted away. The collected gel was calcined for 4 hours at 550 deg C. The calcined solid had a BET surface area of 16.23 $m^2/g$. The specific performance data for this example are set forth below in Table 8. This example shows the utility of non-nitrogen containing bases for the formation of catalytically interesting materials. Although potentially functional the tested materials appear to be inferior to those produced using nitrogen containing bases.

TABLE 8

Additional Preparation Methods for Lanthanum Containing Compositions

| Example | 26 | 27 | 28 | 29 | 30 | 31 |
|---|---|---|---|---|---|---|
| Feed mole ratios | | | | | | |
| $C_2H_4$ | 3.6 | 3.7 | 3.6 | 3.7 | 3.7 | 3.7 |
| HCl | 2.0 | 2.0 | 2.0 | 2.0 | 2.0 | 2.0 |
| $O_2$ | 1.0 | 1.0 | 1.0 | 1.0 | 1.0 | 1.0 |
| He + Ar | 0.2 | 0.2 | 0.2 | 0.2 | 0.2 | 0.2 |
| T (° C.) | 401 | 400 | 400 | 399 | 400 | 401 |
| Space time (s) | 8.6 | 20.8 | 4.7 | 8.7 | 6.2 | 20.0 |
| Fractional conversions (Percent) | | | | | | |
| $C_2H_4$ | 18.8 | 8.7 | 15.6 | 17.4 | 21.0 | 9.3 |
| HCl | 35.8 | 7.7 | 20.0 | 41.5 | 48.4 | 22.3 |
| $O_2$ | 53.0 | 32.6 | 48.8 | 50.6 | 56.8 | 17.9 |
| Selectivities (Percent) | | | | | | |
| VCM | 73.4 | 26.0 | 72.1 | 76.8 | 77.6 | 17.5 |

TABLE 8-continued

Additional Preparation Methods for
Lanthanum Containing Compositions

| Example | 26 | 27 | 28 | 29 | 30 | 31 |
|---------|-----|------|------|-----|-----|------|
| $C_2H_4Cl_2$ | 8.7 | 11.9 | 7.1 | 7.3 | 7.8 | 46.2 |
| $C_2H_5Cl$ | 3.5 | 22.7 | 5.6 | 4.2 | 2.9 | 25.6 |
| $CO_x$ | 9.8 | 38.6 | 12.7 | 7.6 | 6.3 | 9.1 |

Example 32

To further demonstrate the utility of the composition, 1,2-dichloroethane was dehydrochlorinated to yield vinyl chloride by use of the composition as a catalyst. A solution of $LaCl_3$ in water was prepared by dissolving one part of commercially available hydrated lanthanum chloride (purchased from Avacado Research Chemicals Ltd.) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination in air at 550 deg C. for four hours. The resulting solid was crushed and sieved. The sieved particles were placed in a pure nickel (alloy 200) reactor. The reactor was configured such that 1,2-dichloroethane and helium could be fed to the reactor. Space time is calculated as the volume of catalyst divided by the flow rate. Feed rates are molar ratios. The composition was heated to 400 deg C. and treated with a 1:1:3 $HCl:O_2:He$ mixture for 2 hours prior to the start of operation. The reactor system was operated with ethane and ethylene containing feeds to produce vinyl chloride for 134 hours at a temperature of 400 deg C. At this time the feed composition was altered to contain only He and 1,2-dichloroethane in a 5:1 ratio with the temperature at 400 deg C.: Flow was adjusted to yield a 16.0 second space time. Product analysis showed greater than 99.98 percent conversion of 1,2-dichloroethane with the molar vinyl chloride selectivity in excess of 99.11 percent. After 4.6 hours on stream the experiment was terminated. Analysis of the product stream at this time showed conversion of 1,2-dichloroethane to be 99.29 percent with molar selectivity to vinyl chloride of greater than 99.45 percent.

Other embodiments of the invention will be apparent to the skilled in the art from a consideration of this specification or practice of the invention disclosed herein. It is intended that the specification and example be considered as exemplary only, with the true scope and spirit of the invention being indicated by the following claims.

What is claimed is:

1. A process for producing vinyl chloride from ethylene comprising:
   (a) combining reactants including ethylene, an oxygen source, and a chlorine source in a reactor containing a catalyst under conditions sufficient to produce a product stream comprising vinyl chloride, ethylene, and hydrogen chloride; the catalyst consisting essentially of one or more rare earth materials, with the proviso that the catalyst is substantially free of iron, copper, and manganese, and with the further proviso that when cerium is present, the catalyst further consists essentially of at least one more rare earth element other than cerium; and
   (b) recycling ethylene from the product stream back for use in Step (a).

2. A process for producing vinyl chloride from ethylene comprising:
   (a) combining reactants including ethylene; an oxygen source, and a chlorine source in a reactor containing a catalyst under conditions sufficient to produce a product stream comprising vinyl chloride, ethylene, and hydrogen chloride; the catalyst comprising a composition of the formula MOCl or $MCl_3$, wherein M is a rare earth element or mixture of rare earth elements selected from lanthanum, cerium, neodymium, praseodymium, dysprosium, samarium, yttrium, gadolinium, erbium, ytterbium, holmium, terbium, europium, thulium, and lutetium, with the proviso that the catalyst is substantially free of iron, copper, and manganese, and with the further proviso that when cerium is present, the catalyst further comprises at least one more rare earth element other than cerium, and
   (b) recycling ethylene from the product stream back for use in Step (a).

3. The process of claim 2, wherein the chlorine source is a gas and comprises at least one of the following: hydrogen chloride, chlorine, a chlorinated hydrocarbon containing labile chlorines, and mixtures thereof.

4. The process of claim 2, wherein ethane is also combined with the ethylene, oxygen source, and chlorine source in the reactor.

5. The process of claim 4, wherein the total moles per minute of ethylene entering the reactor is substantially equal to the total moles per minute of ethylene leaving the reactor in the product stream, and further wherein substantially all of the ethylene leaving the reactor is recycled.

6. The process of claim 4 wherein any ethane present in the product stream is also recycled back for use in Step (a) of the process.

7. The process of claim 4 wherein, in Step (b), hydrogen chloride from the product stream is also recycled back for use in Step (a) of the process.

8. The process of claim 2 wherein, in Step (b), hydrogen chloride from the product stream is also recycled back for use in Step (a).

9. The process of claim 4 wherein the product stream contains carbon monoxide and carbon monoxide is recycled from the product stream back for use in Step (a) of the process.

10. The process of claim 2 wherein the product stream contains carbon monoxide and carbon monoxide is recycled from the product stream back for use in Step (a).

11. The process of claim 2 wherein substantially no cerium is present in the catalyst.

12. The process of claim 2 wherein the rare earth material component of the catalyst is based on lanthanum, neodymium, praseodymium or mixtures of one or more of these.

13. The process of claim 12 wherein the rare earth material component of the catalyst is based on lanthanum.

14. The process of claim 2, wherein the catalyst is a porous, bulk catalyst.

15. The process of claim 4 wherein the catalyst is a porous, bulk catalyst.

16. The process of claim 15 wherein the catalyst further comprises an element selected from alkaline earths, boron, phosphorous, titanium, zirconium, hafnium, and combinations thereof.

17. The process of claim 15 wherein the catalyst is input to the reactor as a bulk MOCl salt, where M is a rare earth element or mixture of rare earth elements from lanthanum, cerium, neodymium, praseodymium, dysprosium, samarium, yttrium, gadolinium, erbium, ytterbium, holmium, terbium, europium, thulium and lutetium, with the proviso that when cerium is present the catalyst further comprises at least one more rare earth element other than cerium.

18. The process of claim 17, wherein the catalyst input to the reactor is a bulk LaOCl catalyst.

19. The process of claim 2 wherein the temperature in the reactor is maintained between 350° C. to 500° C.

20. The process of claim 2, wherein the catalyst employed is characterized as being water-soluble after a period of use in the process.

21. The process of claim 2 wherein the catalyst is provided in the form of MOCl and has a BET surface area of at least about 12 m$^2$/g.

22. The process of claim 21 wherein the catalyst has a BET surface area of at least about 30 m$^2$/g.

23. The process of claim 21 wherein the catalyst is prepared by a process comprising:
   (a) preparing a solution of a chloride salt of the rare earth element or elements in a solvent comprising either water, an alcohol, or mixtures thereof;
   (b) adding a nitrogen-containing base to cause the formation of a precipitate; and
   (c) collecting, drying and calcining the precipitate in order to form the MOCl composition.

24. The process of claim 2 wherein the catalyst is provided in the form of MCl$_3$ and has a BET surface area of at least about 5 m$^2$/g.

25. The process of claim 24 wherein the catalyst has a BET surface area of at least about 30 m$^2$/g.

26. The process of claim 24 wherein the catalyst is prepared by a method comprising:
   (a) preparing a solution of a chloride salt of the rare earth element or elements in a solvent comprising either water, an alcohol, or mixtures thereof;
   (b) adding a nitrogen-containing base to cause the formation of a precipitate;
   (c) collecting, drying and calcining the precipitate in order to form an MOCl composition; and
   (d) contacting the calcined precipitate with a chlorine source so as to form the MCl$_3$ composition.

* * * * *